United States Patent
Jangir

(10) Patent No.: US 10,376,402 B2
(45) Date of Patent: Aug. 13, 2019

(54) BELT SYSTEM FOR BODY SUPPORT

(71) Applicant: Ganesh Ram Jangir, Jaipur (IN)

(72) Inventor: Ganesh Ram Jangir, Jaipur (IN)

(*) Notice: Subject to any disclaimer, the term of this patent is extended or adjusted under 35 U.S.C. 154(b) by 596 days.

(21) Appl. No.: 15/107,914

(22) PCT Filed: Dec. 17, 2015

(86) PCT No.: PCT/IN2015/059722
§ 371 (c)(1),
(2) Date: Jun. 23, 2016

(87) PCT Pub. No.: WO2016/098039
PCT Pub. Date: Jun. 23, 2016

(65) Prior Publication Data
US 2016/0317340 A1    Nov. 3, 2016

(30) Foreign Application Priority Data

Dec. 18, 2014    (IN) .......................... 3750/DEL/2014

(51) Int. Cl.
*A61F 5/01* (2006.01)
*A61H 3/00* (2006.01)
(Continued)

(52) U.S. Cl.
CPC .............. *A61F 5/0102* (2013.01); *A41D 1/02* (2013.01); *A41F 9/00* (2013.01); *A61H 1/024* (2013.01);
(Continued)

(58) Field of Classification Search
CPC ............ A61F 5/0102; A61F 2005/0167; A61F 2005/0179; A41D 1/02; A41F 9/00;
(Continued)

(56) References Cited

U.S. PATENT DOCUMENTS 4,632,096 A   12/1986   Harris
5,016,869 A    5/1991   Dick et al.
(Continued)

FOREIGN PATENT DOCUMENTS

IN     2155/DEL/2008    4/2010

OTHER PUBLICATIONS

Haohan Zhang, Design of a Passive Exoskeleton Spine, ScholarWorks@UMass Amherst, May 2014.
(Continued)

*Primary Examiner* — Christopher D. Prone
*Assistant Examiner* — Tiffany P Shipmon

(57) ABSTRACT

The present invention is a mechanical assembly for single point torque adjustment, an apparatus and method of use of an improved belt for body support and for assisting body during musculoskeletal activities like heavy lifting, kneeling, bending and walking. The belt employs the single point torque adjusting mechanical assembly with an adjustable hinge along with resilient means which stores potential energy when the user alters from a neutral position and may help the body to return to the neutral position. The belt employs structure to share and direct load from head, neck and back to waist and ground. The apparatus may prevent the user from acquiring spondylitis, kyphosis or osteoporosis. The apparatus may be used for users who are subjected to frequent muscular work like bending up and down while carrying heavy loads, sitting too long, walking and the like.

16 Claims, 8 Drawing Sheets

(51) Int. Cl.
*A61H 1/02* (2006.01)
*B25J 9/00* (2006.01)
*A41D 1/02* (2006.01)
*A41F 9/00* (2006.01)

(52) U.S. Cl.
CPC ............ *A61H 1/0244* (2013.01); *A61H 3/00* (2013.01); *B25J 9/0006* (2013.01); *A61F 2005/0167* (2013.01); *A61F 2005/0179* (2013.01); *A61H 2201/1261* (2013.01); *A61H 2201/163* (2013.01); *A61H 2201/165* (2013.01); *A61H 2201/1616* (2013.01); *A61H 2201/1642* (2013.01)

(58) Field of Classification Search
CPC ........ A61H 1/024; A61H 1/0244; A61H 3/00; A61H 2201/1261; A61H 2201/1616; A61H 2201/163; A61H 2201/1642; A61H 2201/165; B25J 9/0006
See application file for complete search history.

(56) References Cited

U.S. PATENT DOCUMENTS

| | | | |
|---|---|---|---|
| 5,147,261 A | 9/1992 | Smith et al. | |
| 6,016,869 A | 1/2000 | Burts, Jr. | |
| 6,041,444 A | 3/2000 | Mckinney | |
| 7,041,074 B1* | 5/2006 | Averianov | A61F 5/0102 128/845 |
| 7,341,025 B1* | 3/2008 | Streeter | A47D 13/046 119/770 |
| 7,553,266 B2 | 6/2009 | Abdoli-Eramaki | |
| 8,177,733 B2 | 5/2012 | Ashihara et al. | |
| 8,568,344 B2 | 10/2013 | Ferguson et al. | |
| 9,022,956 B2 | 5/2015 | Kazerooni et al. | |
| 9,808,073 B1* | 11/2017 | Maxwell | B25J 9/0006 |
| 2002/0082711 A1* | 6/2002 | Kuhn | A61F 2/604 623/27 |
| 2008/0154165 A1 | 6/2008 | Ashihara et al. | |
| 2011/0004322 A1* | 1/2011 | Sankai | A61H 3/008 623/25 |
| 2011/0098617 A1 | 4/2011 | Ferguson | |
| 2011/0105966 A1* | 5/2011 | Kazerooni | A61H 3/008 601/35 |
| 2014/0200491 A1* | 7/2014 | Julin | A61H 3/00 601/35 |
| 2014/0358053 A1* | 12/2014 | Triolo | A61H 3/00 602/16 |
| 2015/0018739 A1* | 1/2015 | Threlfall | A61H 3/02 602/23 |
| 2015/0025423 A1* | 1/2015 | Caires | A61H 1/024 601/35 |
| 2015/0057587 A1* | 2/2015 | Walsh | A61F 5/0123 602/16 |
| 2015/0321342 A1* | 11/2015 | Smith | B25J 9/0009 74/490.03 |
| 2015/0351995 A1* | 12/2015 | Zoss | A61H 1/024 623/32 |
| 2016/0030272 A1* | 2/2016 | Angold | A61H 1/024 623/24 |
| 2016/0184165 A1* | 6/2016 | Ohta | A61H 3/00 623/27 |
| 2016/0331625 A1* | 11/2016 | Sankai | B25J 9/0006 |
| 2017/0035640 A1* | 2/2017 | Hyung | A61H 3/00 |
| 2018/0272524 A1* | 9/2018 | Ohtsubo | A61H 1/024 |
| 2019/0091093 A1* | 3/2019 | Lee | A61H 3/00 |

OTHER PUBLICATIONS

Herbert Eriksson Och Martin Paulsen, Active Lumbar Assistive Device, Development of new kind of assistive device to reduce the risk of low back pain associated with manual lifting conditions, Jun. 7, 2011.

* cited by examiner

BELT SYSTEM FOR BODY SUPPORT

CROSS-REFERENCE TO RELATED APPLICATIONS AND PRIORITY

The present application does claim priority from Indian provisional patent application number 3750/DEL/2014 dated 18 Dec. 2014.

TECHNICAL FIELD

The present invention relates to a single point torque adjusting mechanical assembly. More particularly, the invention pertains to an apparatus with single point torque adjusting mechanical assembly, and an adjustable hinge connectively coupled with resilient means to reduce human effort, assist knees and waist in order to share such load from head, back, spine, waist and knees and transfer load to ground.

BACKGROUND

The framework of human body is composed of many bones, tendons and ligaments joined together to produce a perfect frame. Spine is very vital part of the human body whose function comprises body support, support for head, movement, protection of spinal cord, co-ordination and control. Support for head is paramount because the neck is involved in quick co-ordinating movements for general daily activities. Protection of spinal cord from jerks, shocks and strains is crucial in maintaining whole body health.

In addition to the healthy spinal cord, all body joints along with ligaments and tendons are required to be in good condition to maintain proper posture, effective movement or locomotion.

People involved in activities like regular lifting or carrying of weight, carrying weight over head or back, or doing other similar hardships are exposed to frequent bending and retracting of the body parts that may result in disorders comprising waist pain, knee pain, neck pain, vertebral dislocation and the like due to straining and stretching of body parts. Constant laborious work with too much bending, kneeling and walking may lead also lead to disorders like spondylitis, kyphosis or inflammation. Some people may also acquire osteoporotic spine which changes the shape of the spine itself.

Such disorders are treated by use of high doses of pain killers or by employment of fixed web structures, elastic belts which are usually wrapped around the susceptible body parts. It is often the strategy to support spine and waist by tying up straps around them; however, this may restrict the body motion partly or wholly. Such a solution may also not assist spine or waist completely.

Thus there exists a long felt need for a solution which not only assists the person in lifting heavy objects but also supports his bent position, sitting posture, carrying load over back and head, long distance walking and can be used as corrective measure for spinal disorders like spondylitis, kyphosis and inflammation.

In a prior art a Patent application number US20080154165 proposes mainly body weight support device with a floor contact member. This externally powered and legs centric device is very heavy due to the presence of actuator, drive units and other auxiliary components. The Indian Patent application number 2155/DEL/2008 filed by the inventor of this patent itself proposes a belt that does not have attachable members like leg apparatus, structure for sharing load from head, waist, back to ground, single point torque adjustment mechanical assembly. Another prior art U.S. Pat. No. 6,041,444 proposes load supporting waist belt for supporting the weight of the user himself, however the disclosed belt does not assist walking or reducing the total or partial load being carried or displaced by user. U.S. Pat. No. 4,632,096 proposes same function but only for bracing or supporting knees. The invention disclosed in U.S. Pat. No. 5,147,261 may help in lifting by constraining the lumbar region by a flexible belt with no other unique mechanism. The device disclosed in U.S. Pat. No. 6,016,869 is a pedalling, heavy and bulky device for lift assisting.

The above mentioned prior inventions in this domain have not disclosed a lightweight apparatus with single point assisting torque adjustment mechanism, which is self-powered, light weight, compact yet efficient, simple and user friendly apparatus which not only assists the person in lifting heavy objects but also supports his kneeling position, bent position, lateral bending, sitting posture, carrying load overhead, back, long distance walking and can be used as corrective measure for spinal disorders like spondylitis, kyphosis or inflammation and easy to be worn by a user and is effective in reducing the effort of the human body to carry out various voluntary muscular action with full freedom of movement of the body parts.

SUMMARY

Before the present apparatus and its components and its method of use is described, it is to be understood that this disclosure is not limited to the particular apparatus and its arrangement as described, as there can be multiple possible embodiments which are not expressly illustrated in the present disclosure but may still be practicable within the scope of the invention as determined by claims. It is also to be understood that the terminology used in the description is for the purpose of describing the particular versions or embodiments only, and is not intended to limit the scope of the present application. This summary is not intended to identify essential features of the claimed subject matter nor is it intended for use in detecting or limiting the scope of the claimed subject matter.

In one aspect the invention is a single point torque adjusting mechanical assembly wherein mechanical assembly varies the torque non linearly by adjusting a lever arm length such that fixed end of a resilient means need not be displaced; the said mechanical assembly comprising of an upper element, a lower element, resilient means with fixed end and free end, flexible inextensible element or rope, hinge pin and shaft, load/torque adjusting means having a single point at its free end. The mechanical assembly is such that the upper element is moveably secured with lower element by the hinge pin and shaft, and one end of the load adjusting means is moveably connected with a secured end of upper element. The flexible inextensible element or rope is moveably secured with/between the free end of the resilient means and hinge pin and such flexible inextensible element passes through the free end of the load adjusting means. The length of flexible inextensible element or rope is equivalent or equal to sum of distance between hinge pin and free end of load adjusting means and distance between free end of load adjusting means and the free end of the resilient means. The sum of such distance remains constant.

In another aspect, the invention relates to an apparatus for assisting musculoskeletal activities wherein the apparatus enables a user to overcome the effort required to return to a neutral position by employing a counter torque, by storing potential energy in a resilient means. The apparatus comprises one or more longitudinal mechanical elements, an adjustable hinge mechanism means; one or more resilient means; an arrangement for height and torque load adjustment means; and one or more straps for waist, back or shoulders as well as a thigh element moveably and flexibly connected to straps. The apparatus as a whole is characterized by single point torque adjusting mechanical assembly so that the counter torque is developed when the user alters the body posture from the neutral position by performing musculoskeletal activities which results in the potential energy being stored in the resilient means. The single point torque adjusting mechanical assembly incorporated with adjustable hinge attached to a resilient means is responsible for generating a counter torque to bring back the user to the neutral position. The counter torque can be non-linearly varied using single point torque adjusting mechanical assembly for adjusting distance between hinge and a single point, wherein the hinge acts as an axis of rotation and said longitudinal distance acts as lever arm. The single point torque adjusting mechanical assembly incorporated with adjustable hinge are used for spine, pelvic and knee joints and has extended arrangements to use the single point torque adjusting mechanical assembly. In another aspect the apparatus also has attachable structure to share the load from head, spine and back in order to transfer the shared load to waist and ground. Thus transferring the load on head and back to the ground.

In yet another aspect the invention relates to a method for assisting musculoskeletal activities using an apparatus wherein the apparatus enables a user to overcome the effort required to return to a neutral position by employing a counter torque by storing potential energy in a resilient means. The method as a whole may be performed in a manner that the counter torque is developed when the user alters the body posture from the neutral position by performing musculoskeletal activities which results in the potential energy being stored in the resilient means. The single point torque adjusting mechanical assembly incorporated with adjustable hinge attached to a resilient means are responsible for generating a counter torque to bring back the user to the neutral position. The counter torque can be non-linearly varied using single point torque adjusting mechanical assembly by adjusting distance between hinge and single point, wherein the hinge acts as an axis of rotation and said longitudinal distance acts as lever arm. The single point torque adjusting mechanical assembly incorporated with adjustable hinge are used for pelvic and knee joints and has extended arrangements to use the single point torque adjusting mechanical assembly. Apparatus also has attachable structure to share the load from head, spine and back in order to transfer the shared load to waist and ground. Thus transferring the load on head and back to the ground.

In yet another aspect the invention is also directed to an apparatus for assisting musculoskeletal activities wherein the apparatus enables a user to share load on body parts and transfer such load to the ground, the said apparatus comprising one or more straps/belts for waist 111, back 107 or shoulders 106; and one or more body adaptable shoulder element 101, thigh element 102, leg element 103 and a structure 601 having a body adaptable shaped profile to carry loads wherein upper side of structure is mounted at back strap 107 using moveable securing means characterized in that the structure 601 may form a platform or a cantilever beam which may transmit the load at the head to the belt and further the belt may transfer the load to the leg and finally to the ground.

BRIEF DESCRIPTION OF DRAWINGS

The detailed description is described with reference to the accompanying Figures. In the Figures, the left-most digit(s) of a reference number identifies the Figure in which the reference number first appears. The same numbers are used throughout the drawings to refer like features and components.

DETAILED DESCRIPTION

The present invention relates to an apparatus and method embodying an improved belt for body support and for assisting body during heavy lifting, kneeling, bending and walking. More particularly, the belt (referred also as apparatus at various instances in the specification) employs a single point torque adjusting mechanical assembly with an adjustable hinge along with resilient means which stores potential energy when the user alters posture from a neutral position and helps the body to return to the neutral position.

For the purpose of this invention "neutral posture" may be a posture where the joints are not bent and the spine and legs are aligned and are not twisted. The words "load", "torque" and "assisting torque" are used interchangeably and point to similar meaning.

For the purpose of this invention "resilient means" may be an object which is capable to recoil or spring back into shape after bending, stretching or being compressed. Resilient means may comprise a spring, hydraulics pneumatics, elastic strand, elastic rope, band and the like. In one embodiment of the invention the resilient means may be powered or unpowered.

For the purpose of this invention "musculoskeletal activities" may comprise human actions further comprising kneeling, sitting, walking, running, up/down bending, bending forward/backward and left/right rotation, carrying and picking the load, and other similar activities for various durations and frequency.

For the purpose of the invention the words System and Apparatus are also interchangeably used.

For the purpose of this invention, all results in tables, graphs or numbers comprising torque, load, angles in degrees, length and the like included are to be considered in the range of ±10% of the given value. For example, a torque of 100 N-cm should be considered in the range of 90 N-cm to 110 N-cm. It is to be understood that graphical or numerical data is based on a prototype developed with particular set of embodiments and arrangements as described, but does not limit the apparatus and method as there can be multiple possible embodiments, settings and arrangements which are not expressly illustrated in the present disclosure.

Figure 1:
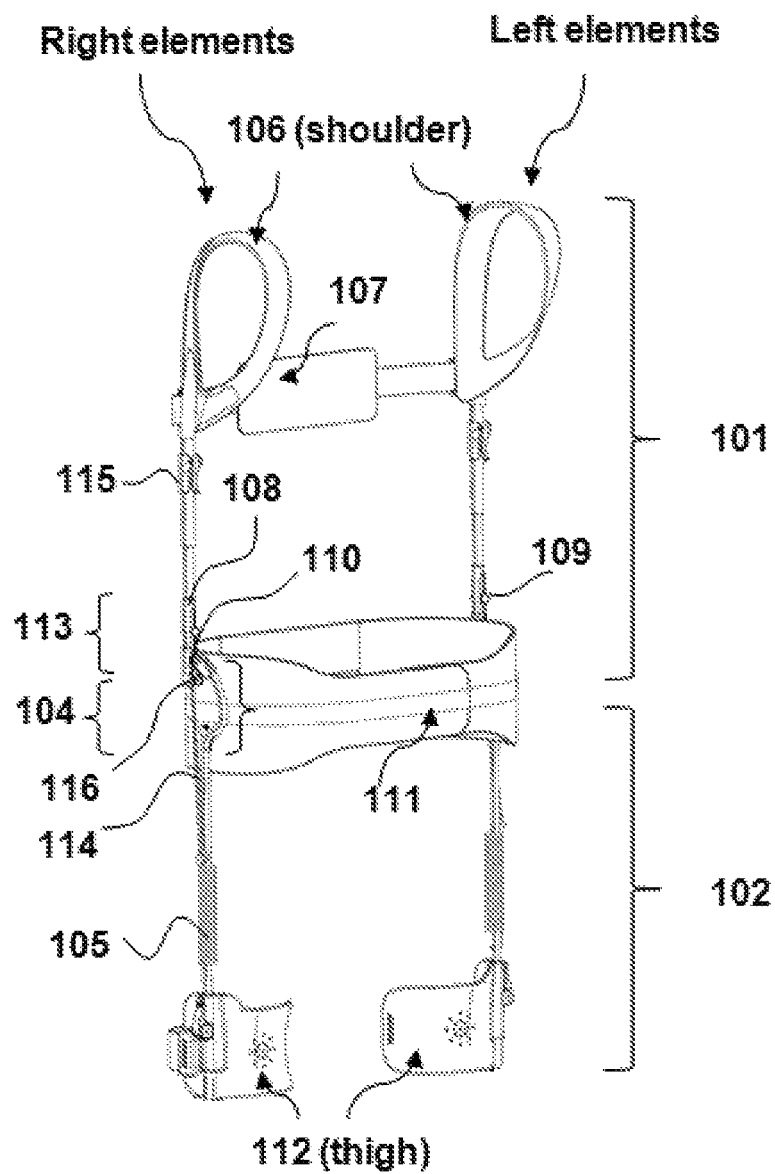
FIG. 1A illustrates a representation of the apparatus belt in accordance with an embodiment of the present subject matter.
FIG. 1B illustrates a representation of the apparatus belt with an attachable leg apparatus/element.
Figure 1:
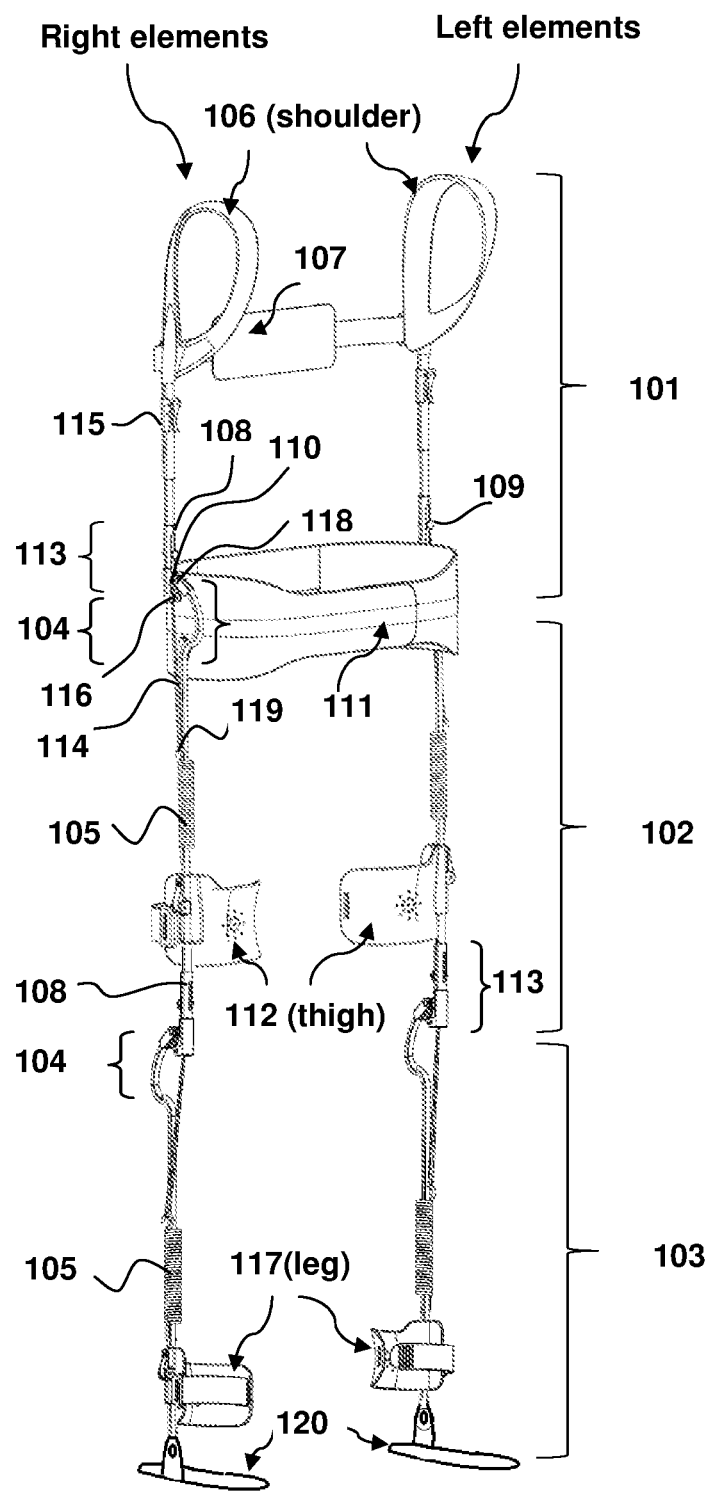

Referring to FIG. 1 A, a representation of the belt is illustrated in accordance with an embodiment of the present invention. Element at left side of user may be called as left-element and the element at the right side of user may be called as right-element. Each longitudinal element may be made of at least two or three sub-elements having enlargement and engagement-disengagement arrangement. Upper sub-element attached with shoulder may be called as Shoulder-element 101, sub-element attached with thigh may be called as thigh-element 102. Each sub-element of a longitudinal element is adjustable in size and may be connected via one or two hinge mechanism 104 connectively coupled with single point torque/load adjusting mechanical assembly 113 and having resilient means 105 or powered resilient means or both. Upper end of shoulder element 101 may have cushioned strap 106 and the lower end of the shoulder element 101 is connected to upper end of thigh-element 102 via a hinge and single point torque adjusting mechanical assembly 104. The cushioned strap 106 may grip the shoulder and the shoulder element 101 together. Shoulder element 101 of both sides may be connected via resilient element called back strap 107. Upper-end of the Shoulder element 101 may have an arrangement of adjusting the length of the Shoulder-element 101 and has flexibility and size adjustment mechanism 115 to make it ergonomically comfortable. The mentioned hinge mechanism 104 is connectively coupled with single point torque/load adjusting mechanical assembly 113 which movably may connect the lower end of shoulder element 101 and upper end of thigh-element 102.

The hinge mechanism comprises of a load adjusting pipe 108 moveably attached with lower end of shoulder element 101 and has button 109 mechanism to fix load adjusting pipe 108 at a particular position. Particular position of load adjusting pipe 108 determines the load and torque of the hinge mechanism. An inextensible and flexible element or rope 114 connects upper end of resilient means 105 or powered resilient means to the hinge-pin 110 and passes via single point 116 located at lower end of load adjusting pipe 108. Hinge pin 110 may be a part of hinge mechanism fixed with lower end of shoulder-elements 101 and may movably connect to shaft 118 of the hinge. The other end of resilient element 105 or powered resilient element may be fixed to the lower end of the thigh-element 102.

In an embodiment, when the user bends down, the apparatus may generate a force of tension in inextensible and flexible elements which transfer the load to resilient means 105. Thus the potential energy gets stored in resilient means 105 and the hinge mechanism 104 connectively coupled with single point torque/load adjusting mechanical assembly 113 may provide counter support to user's back and waist through the waist strap. The stored potential energy assists the user when user tends to bend-up and stand up. Different positions of mentioned load adjusting pipe 108 or different combination of r and 1 ensure the different length of lever arm of the hinge and make different elongations to resilient means 105. If load adjusting pipe 108 is positioned to increase lever arm length, then the hinge may provide more counter torque or increase the counter load resulting the hinge to bear more load and vice-versa. The length of flexible inextensible element or rope 114 is equivalent to sum of lengths of r (OA) and l (AB) and remain same for different lever arm length. Each of the thigh elements 102 or longitudinal element may be movably connected with the waist belt 111. Waist belt 111 may be cushioned flexible element meant to wrap around the waist or body of the user. It may connect both longitudinal elements at the waist together and to the waist of user. Lower end of thigh-element 102 has pad like structure and cushioned straps 112 that may grip the thigh-element 102 to the thigh. Pad like structure may be adjusted at different position at thigh-element 102 and have different ergonomics and user friendly shape and arrangement that enable to wear the belt over cloths such as Skirts and Sarees without need of straps or tying around thighs. The lower end of thigh-element 102 is moveably connected to the leg-element 103 via another hinge 104 cum load/torque adjusting mechanical assembly 113 similar to described hinge mechanism 104 connectively couple with single point torque/load adjusting mechanical assembly 113 at lower end of Shoulder-element 101 but later is for knee.

In an implementation, a flexible and adjustable mechanism 115 may be provided above the load adjusting pipe 108 and below the shoulder element 101 to change the height of the apparatus for the concerned user. This mechanism may provide better ergonomics to the apparatus for compliance in the user-apparatus working environment. In another embodiment 502 which lies inside shoulder element 101 with springs or resilient mean, helps in size adjustment and gets compressed when user bends down and return in normal shape when user bend up to ensures shoulder element moves in accordance with shoulder.

Referring FIG. 1 B, the assembly along with the leg element or leg apparatus is illustrated with an embodiment of the present invention. In another embodiment, a mechanism that may also ensure the movement of leg-element 103 during walking and sitting posture of user is disclosed. Lower end of leg-element 103 may have padded and cushioned strap 117 to grip leg-elements 103 with the leg and also have foot element 120 moveably secured with the lower end of leg element 103 to transfer the load and weight to ground. The hinge mechanism 104 that is connectively coupled with single point torque/load adjusting mechanical assembly 113 may support and assist the knees of user. When user sits-down or when he folds the leg by using the knees then the potential energy may get stored in the resilient mean 105 or powered resilient means. The same energy supports the user and assists the user during standing-up or in musculoskeletal activities. This mechanism may have elements connecting shoulder-element 101 to leg-element 103. The leg-element 103 may transfer the weight and load from the user to ground and lower part of body thus minimizing the adverse consequences of lifting heavy load and strenuous activities. Its assists the also when user is half seated, stand up, seats frequently.

In case of a person who is wearing the belt system of the current invention, when such person bends up/down, sits down or stands up while lifting a weight or while such person is doing any other strenuous activity, the strain and stress falling on body part of such person is taken up by the elastic force provided in resilient means 105 resulting in free movement of his back, waist and knee, without running the risk of adverse consequences.

Figures 2A, 2B:
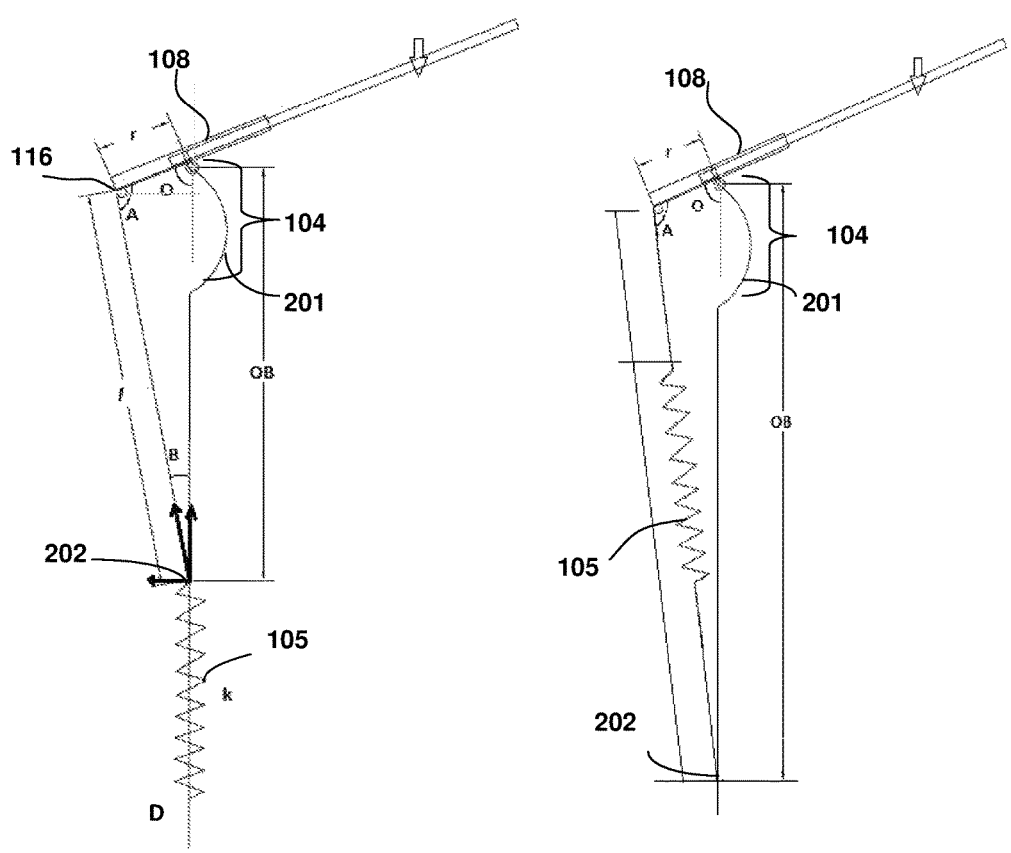
FIGS. 2A and 2B illustrate a method for reducing the effort using the counter torque produced by the hinge mechanism 104 connectively coupled with single point torque/load adjusting mechanical assembly 113 in accordance with an embodiment of the present subject matter.

Referring to FIG. 2A, which illustrates apparatus and methods for reducing the effort using the counter torque produced by the hinge mechanism 104 connectively coupled with single point torque/load adjusting mechanical assembly 113 in accordance with an embodiment of the present subject matter. In an implementation, the upper part of the hinge mechanism 104 connectively coupled with single point torque/load adjusting mechanical assembly 113 may constitute the load adjusting pipe 108 with button 109 mechanism. The load adjusting pipe may have groves or holes in it to engage the button 109 as per the required load. Length OA denotes the lever arm which non-linearly varies the torque and counter torque in the apparatus as torque is directly proportional to lever arm and the force applied. Point O may always remain fixed. The load adjusting pipe 108 may slide over the lower end of shoulder element 101 to change the lever arm length. A flexible inextensible element of length equivalent to sum of AO and AB, passing via single point A, connects Point O of hinge to the upper end B of resilient means 105 or power resilient means which may store the potential energy when the user bends down, kneels down or takes a sitting posture. The stored potential energy may exert a force on load adjusting pipe at the single point A at distance AO from point O which may eventually produce torque due to the lever arm. A single point torque adjusting mechanical assembly 113 adjusts the torque by adjusting the lever arm (r) length such that the lower/second end D of resilient means 105 needs not to be shifted. The length OD and sum of lengths of l and r remains constant; and do not require adjusting pre load/tension in resilient means 105; and comprises of load adjusting pipe 108 and flexible inextensible element or wire rope 114 wherein load adjusting pipe has single point (A) 116 at its lower end. Flexible inextensible element or wire rope 114 of length (l+r) connected to upper end of resilient mean 105 to hinge pin via single point (A) of load adjusting pipe 108. In an exemplary embodiment, a similar mechanism with alternative arrangements of the hinge with the load adjusting pipe 108 and the resilient means 105 is illustrated in FIG. 2B. This configuration may work similar in functionality with FIG. 2A but may have different orientation as shown in FIG. 2B. Referring again to FIG. 1A, the load adjusting pipe 108 can be slide over the lower end of shoulder element 101 and thigh elements 102 to change the lever arm length to produce non-linear variable counter torque to reduce the effort for musculoskeletal actions. The load adjusting pipe 108 can be locked/unlocked with lower end of shoulder element 101 using engagement/disengagement button 109; and optionally comprises of extended mechanism to facilitate locking/unlocking and sliding of load adjusting pipe 108 to adjust the torque; and single point torque adjusting mechanical assembly can be used/applied in other applications such as humanoid, exo-skeletons and other applications and equipments.

Figure 3:
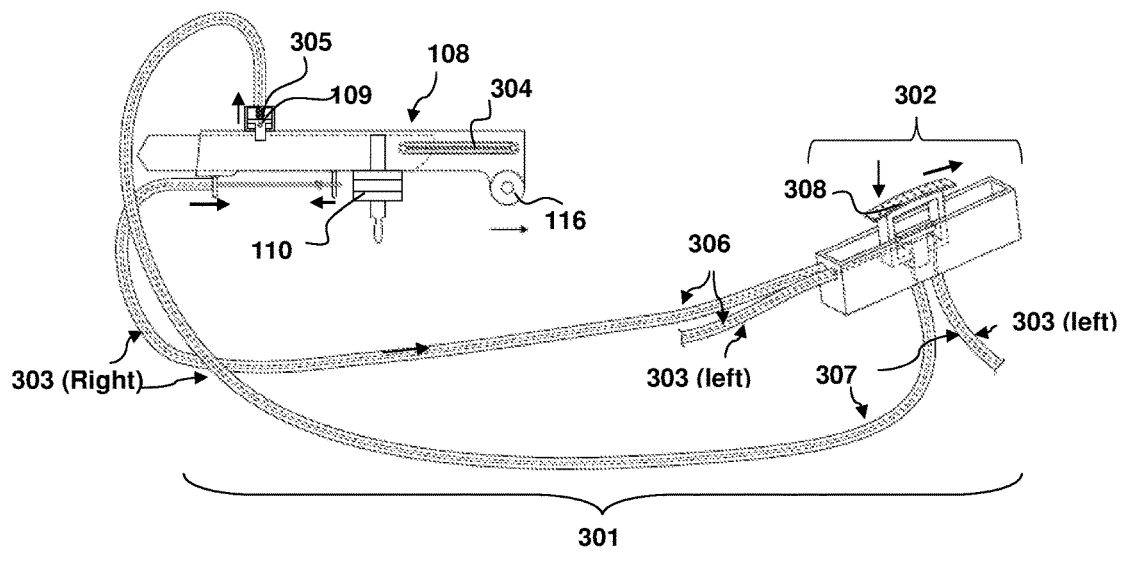
FIG. 3 illustrates an extended mechanism for adjusting load mechanism with an embodiment of the present subject matter.

Referring FIG. 3, an extended mechanism 301 for adjusting load is illustrated with an embodiment of the present subject matter. In an embodiment, the apparatus may be equipped with an extended mechanism 301 to enable the user to adjust the torque by adjusting load pipe 108 and engage/disengage the button 109. The apparatus may comprise one or more extended mechanisms 301 for adjusting load for hinge 104 cum load adjusting mechanical assembly 113 at the waist and another hinge 104 cum load adjusting mechanical assembly 113 at knee for leg element 103. The extended mechanism 301 for adjusting the load may be positioned at the front of waist or elsewhere which may be easily accessible by the user as preferred than that of position where the hinge mechanism 104 connectively coupled with single point torque/load adjusting mechanical assembly 113 is located. The lock mechanism may help the user to adjust the torque.

In an embodiment, the extended mechanism 301 for adjusting the load may comprise a lock element 302, one or more wires 303 connected to the button 109 which passes through the lock element 302 and may be attached to the load adjusting pipe 108 by fastening means, a tension spring 304 connected to a fixed support at one end and the load adjusting pipe 108 at the other end, a compression spring 305 connected to the button 109 such that the compressive force makes the button 109 to insert in the holes or slots in the load adjusting pipe 108. The wires 306 are meant to slide the load pipe 108 and wires 307 are meant for engaging/disengaging button 109. One or more wires 306, 307 may be locked at the locking element 302. In an implementation, when the user pulls the wire 307 by pressing knob 308, it unlocks the button 109 and load adjusting pipe 108 can slide when user moves the knob 308 from the lock element 302. In default condition button 109 is locked due to compression spring 305. Load adjusting pipe 108 is set for minimum lever arm length due to default action of tension spring 304. The button 109 auto engages itself when next or previous slot arrives against it because of the compressive action of the compression spring 305. The tension spring 304 allows load adjusting pipe to return to the minimum position as the tension in the spring forces the load adjusting pipe 108 to come towards hinge pin 110 or toward axis/shaft 118 of rotation of hinge. Thus by the extended mechanism 301 for adjusting the load, the user may adjust the torque and load carrying capacity of the apparatus easily. Wires 303 corresponding to one load adjusting pipe 108 is such that it is one continuous wire 303 though it appears as two wires from the lock element 302. Each one main wire 303 may correspond to their respective left or right load adjusting pipe 108.

Figure 4:
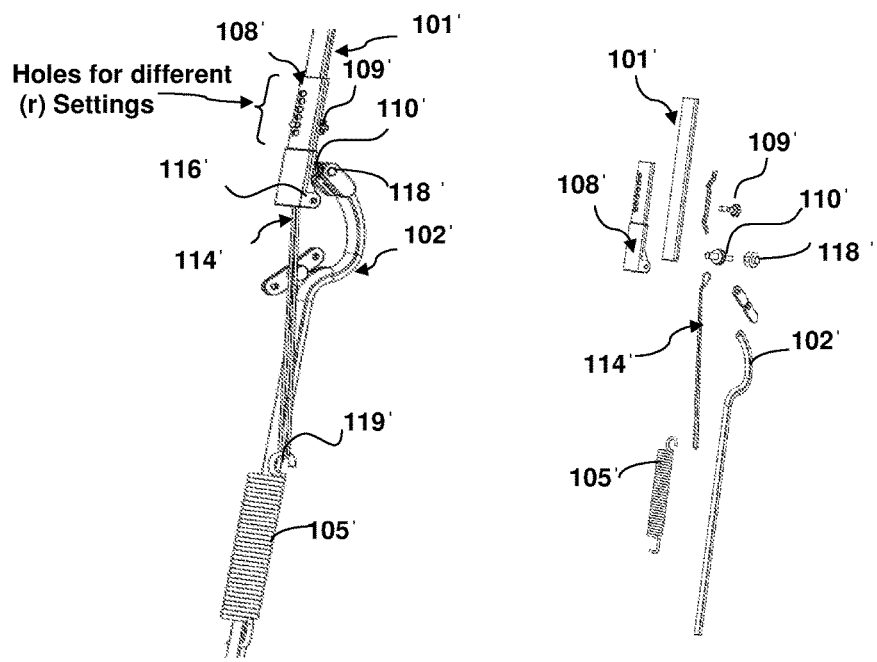
FIG. 4 illustrates a single point torque/load adjusting mechanical assembly with an embodiment of the present subject matter.

Referring FIG. 4, a representation the single point torque/load adjusting mechanical assembly is illustrated with an embodiment of the present invention. A single point torque adjusting mechanical assembly wherein mechanical assembly non-linearly varies the torque by adjusting a lever arm length such that fixed end of a resilient means 105' need not be displaced; the said mechanism comprising of an upper element 101', a lower element 102', resilient means 105' with fixed end and free end 119', flexible inextensible element or rope 114', hinge pin 110' and shaft 118', load/torque adjusting means 113' having a single point at its free end 116'. The mechanical assembly is such that the upper element 101' is moveably secured with lower element 102' by the hinge pin 110' and shaft 118', and one end of the load adjusting means 108 is moveably connected with a secured end of upper element 101'. The flexible inextensible element or rope 114' is moveably secured with/between the free end 119' of the resilient means and hinge pin 110' and such flexible inextensible element 114' passes through the free end 116 of the load adjusting means 105'. The length of flexible inextensible element or rope 114' is equivalent or equal to sum of distance between hinge pin 110' and free end 116' of load adjusting means 108' and distance between free end 116' of load adjusting means and the free end 119' of the resilient means. The sum of such distance remains constant. The said load adjusting means 108' can slide over the lower end of upper element 101' to change the lever arm length to produce non-linear variable counter torque. Hinge pin 110' and shaft 118' can be replaced as a ball and socket joint. The adjustment of pre load/tension in resilient means 105' is not required in this mechanism. The load adjusting means 105' can be locked/unlocked with lower end of upper element 101' using engagement/disengagement means 109'. The mechanism optionally comprises of extended mechanism to facilitate locking/unlocking and sliding of load adjusting means 108' to adjust the torque.

Figure 5:
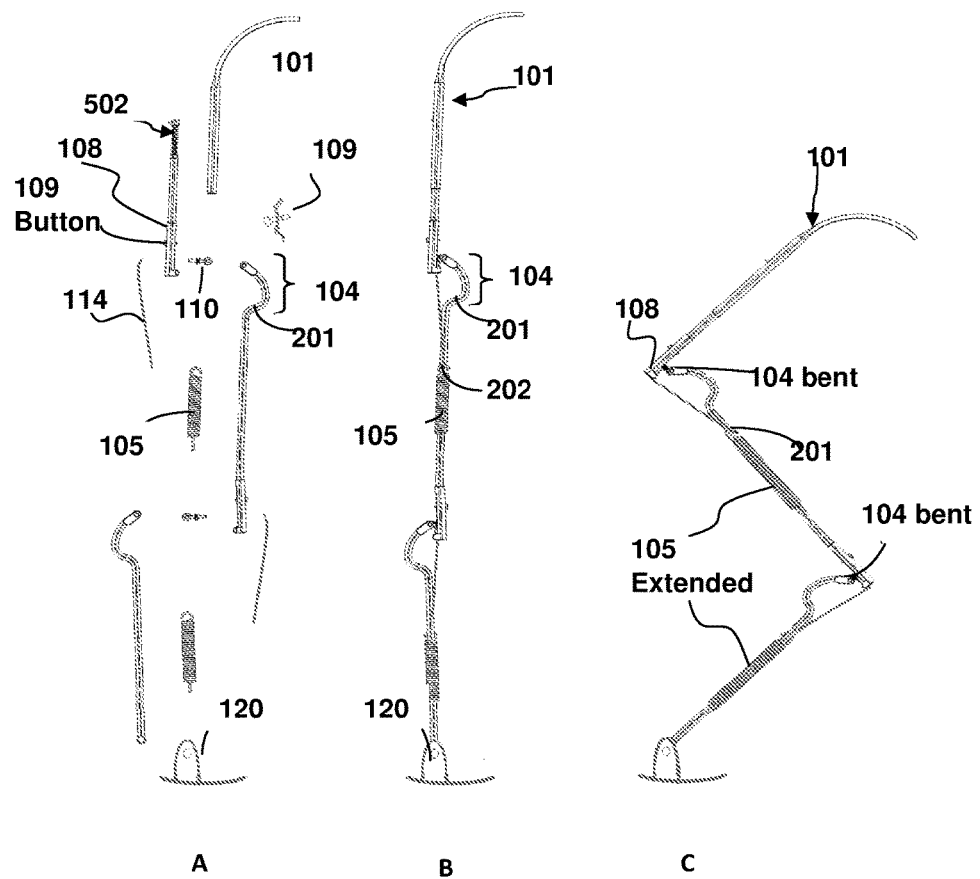
FIG. 5 illustrates various positions of the apparatus with element showing exploded view and assembled view wherein the load transfer from the apparatus to the ground by enabling a foot element 120 with an embodiment of the present subject matter.

Referring FIG. 5, various positions of the apparatus with element showing exploded view and assembled view wherein the load transfer from the apparatus to the ground by enabling a foot element 120 is illustrated with an embodiment of the present subject matter. In an embodiment, the working of the belt is illustrated at various positions with an embodiment of the present subject matter. In FIG. 1-A, an exploded view of the apparatus is represented wherein from the top to the bottom all elements comprising the shoulder element 101, load adjusting pipe 108, button 109, rope 114, hinge 104, resilient means 105, the lower hinge and resilient means and the foot element 120 for transferring the load at the ground. In FIG. 1-B, the assembled apparatus is represented at neutral position with no bending or twisting of any joints or muscles by the user (not shown). The hinges which may be at neutral position or posture may be at zero-degree bend and resilient means 105 may also be in an unloaded position. In FIG. 4-C, the assembled belt is represented along with a sitting posture. The extended leg element 103 may have the foot element 120 which may transfer the load from the body to the leg element 103 and finally to the ground. During this extreme position all the hinges at the waist and the knees and all the resilient means 105 are into action to overcome the load acting on the user.

Figure 6:
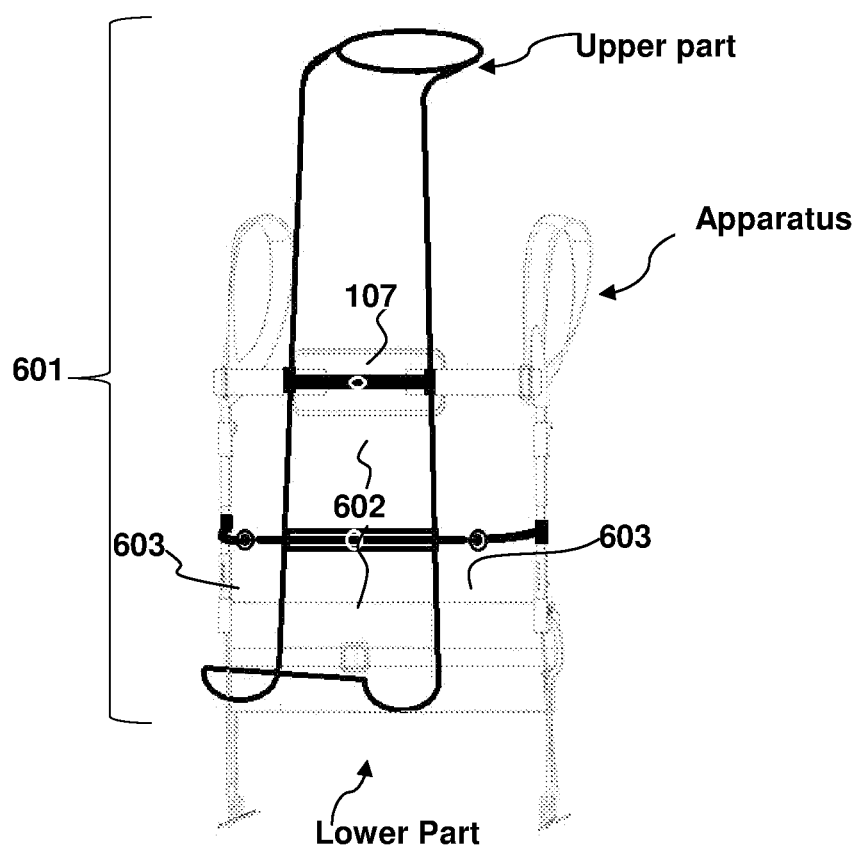
FIG. 6 illustrates an additional structure to carry loads which may be movably secured at the waist and back by belts with an embodiment of the present subject matter.

Referring FIG. 6, an addition of structure 601 to carry loads which may be pivoted at pivot points 602 mechanical element connecting both 3D or simple hinges 603 and upper side of structure is mounted at back strap 107 is illustrated with an embodiment of the present subject matter. In another embodiment, the apparatus may also be equipped by a load carrying structure which may be attached to the back of the apparatus near at mechanical element connecting both 3D hinges 603 and uppers side of structure is mounted at back strap 107. The 3D hinges 603 are mounted on lower end (inner pipe) of shoulder element. The structure 601 may be a continuous Z shaped profile if viewed from the left side of the user. The upper part of the structure 601 may be used to carry load at the head. The upper part of the structure 601 may form a platform or a cantilever beam which may transmit and share the load at the head to the belt and further the belt may transfer the load to the leg and finally to the ground. In an implementation, the load may also be carried at the back with help of the lower platform which may also work as a load carrying beam. The load on the lower part may be transferred to the apparatus by the insertion of the pivot which may join the structure 601 and the apparatus at the pivot point. Heavy lifting of loads comprising sack of grains, cement or any other material may be performed with ease by the apparatus attached with the structure 601. Pivoted at mechanical element connecting both 3d hinges 603 and uppers side of structure is mounted at back strap 107. The 3D hinges 603 are mounted on lower end (inner pipe) of shoulder element.

In an implementation, the attachment of the structure 601 may be so adjusted that the orientation of the structure remains vertical. The structure 601 may be pivoted at pivot points 602 at mechanical element connecting both 3D hinges 603 and uppers side of structure is mounted at back strap 107. The 3D hinges 603 are mounted on lower end (inner pipe) of shoulder element which may enable swivelling of the structure in multi direction when user performs actions comprising flexion, bending, bending with rotation or unlevelled stepping. When user steps up or down the orientation of the structure 601 remains same due to the effect of the 3D hinge or multi directional joint 603. Thus the incorporation of the multi-directional joints 601 results in the correct vertical orientation of the structure even if user' posture may not be vertical.

Figure 7:
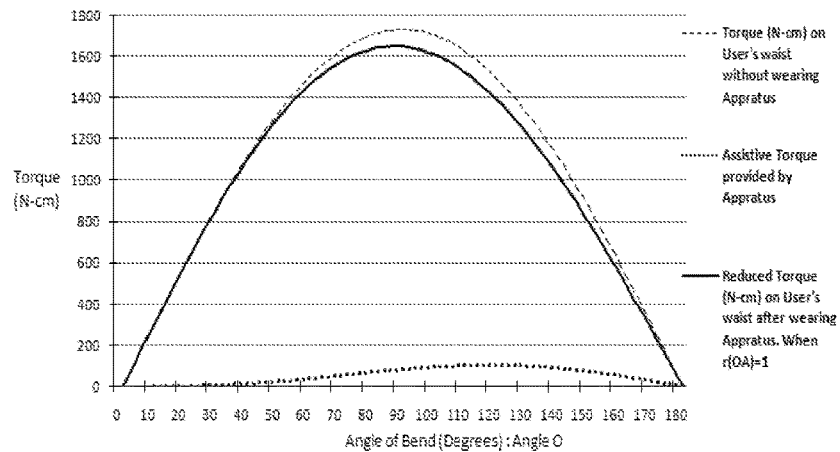
FIG. 7 illustrates results for torque and load when a user incorporates the apparatus with lever arm length 1 cm in accordance with an embodiment of the present subject matter.

Referring to FIG. 7, a representation of non-linear variation of torque with respect to the angle of bend is illustrated and a reduction of load on user's waist is represented with torque on abscissa and angle of bend on ordinate is illustrated as an embodiment of the present subject matter. Following Table 1 represents a data of a user with 70 kg self-weight with height 180 cm and lifting a load of 20 kg with lever arm of 1 cm.

TABLE 1

| Sr. No. | Angle ° (degrees) | Load (N-cm) on User's waist without wearing apparatus | Assistive Torque provided by Apparatus | Reduced Load (N-cm) on User's waist after wearing apparatus. When r(OA) = 1 |
|---|---|---|---|---|
| 1 | 0 | 0 | 0 | 0 |
| 2 | 30 | 865 | 6 | 859 |
| 3 | 60 | 1499 | 37 | 1462 |
| 4 | 90 | 1731 | 83 | 1648 |
| 5 | 120 | 1499 | 103 | 1396 |
| 6 | 150 | 866 | 72 | 793 |
| 7 | 180 | 0 | 0 | 0 |

Figure 8:
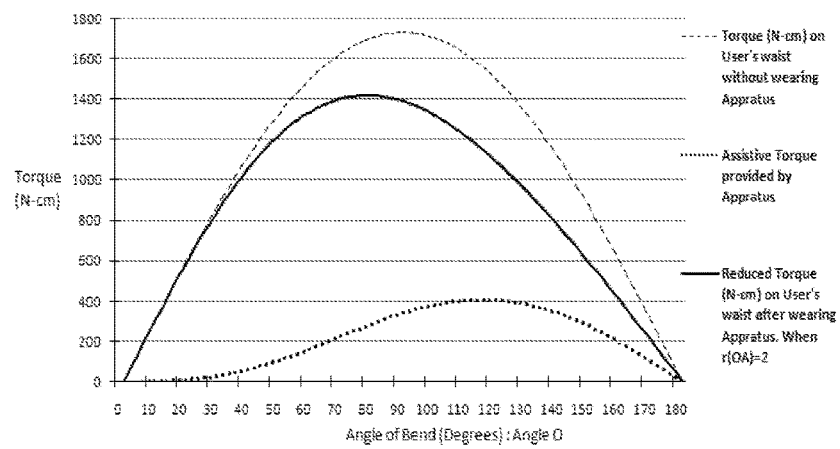
FIG. 8 illustrates results for torque and load when a user incorporates the apparatus with lever arm length 2 cm in accordance with an embodiment of the present subject matter.

Referring to FIG. 8, wherein a representation of non-linear variation of torque with respect to the angle of bend and a reduction of load on user's waist is represented with torque on abscissa and angle of bend on ordinate is illustrated as an embodiment of the present subject matter. Following Table 2 represents a data of a user with 70 kg self-weight with height 180 cm and lifting a load of 20 kg with lever arm of 2 cm.

TABLE 2

| Sr. No. | Angle ° (degrees) | Load (N-cm) on User's waist without wearing apparatus | Assistive Torque provided by Apparatus | Reduced Load (N-cm) on User's waist after wearing apparatus. When r(OA) = 2 |
|---|---|---|---|---|
| 1 | 0 | 0 | 0 | 0 |
| 2 | 30 | 865 | 26 | 839 |
| 3 | 60 | 1499 | 160 | 1339 |
| 4 | 90 | 1731 | 340 | 1391 |
| 5 | 120 | 1499 | 405 | 1094 |
| 6 | 150 | 866 | 27 | 592 |
| 7 | 180 | 0 | 0 | 0 |

Figure 9:
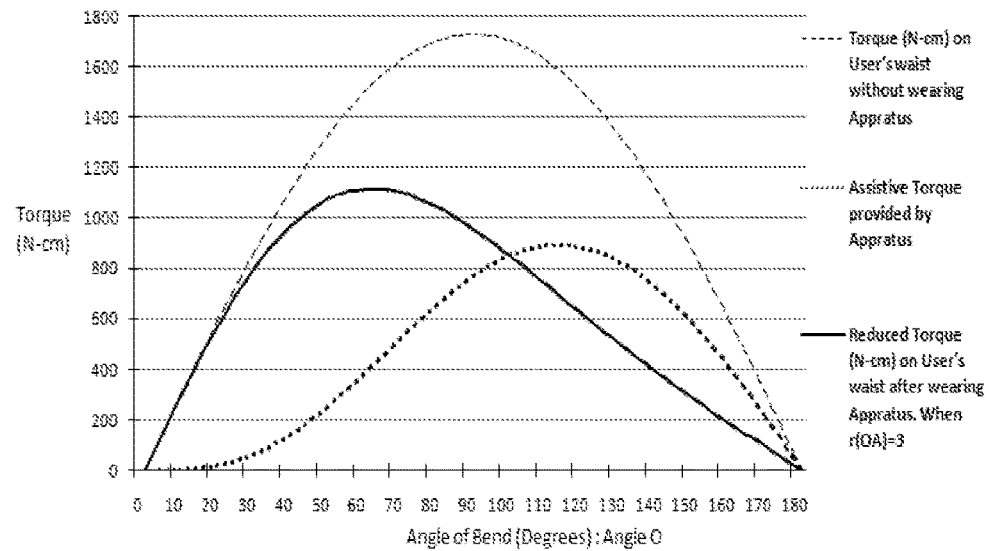
FIG. 9 illustrates results for torque and load when a user incorporates the apparatus with lever arm length 3 cm in accordance with an embodiment of the present subject matter.

Referring to FIG. 9, wherein a representation of non-linear variation of torque with respect to the angle of bend and a reduction of load on user's waist is represented with torque on abscissa and angle of bend on ordinate is illustrated as an embodiment of the present subject matter. Following Table 3 represents a data of a user with 70 kg self-weight with height 180 cm and lifting a load of 20 kg with lever arm of 3 cm.

TABLE 3

| Sr. No. | Angle ° (degrees) | Load (N-cm) on User's waist without wearing apparatus | Assistive Torque provided by Apparatus | Reduced Load (N-cm) on User's waist after wearing apparatus. When r(OA) = 3 |
|---|---|---|---|---|
| 1 | 0 | 0 | 0 | 0 |
| 2 | 30 | 865 | 65 | 800 |
| 3 | 60 | 1499 | 382 | 1117 |
| 4 | 90 | 1731 | 773 | 958 |
| 5 | 120 | 1499 | 884 | 615 |
| 6 | 150 | 866 | 581 | 284 |
| 7 | 180 | 0 | 0 | 0 |

Figure 10:
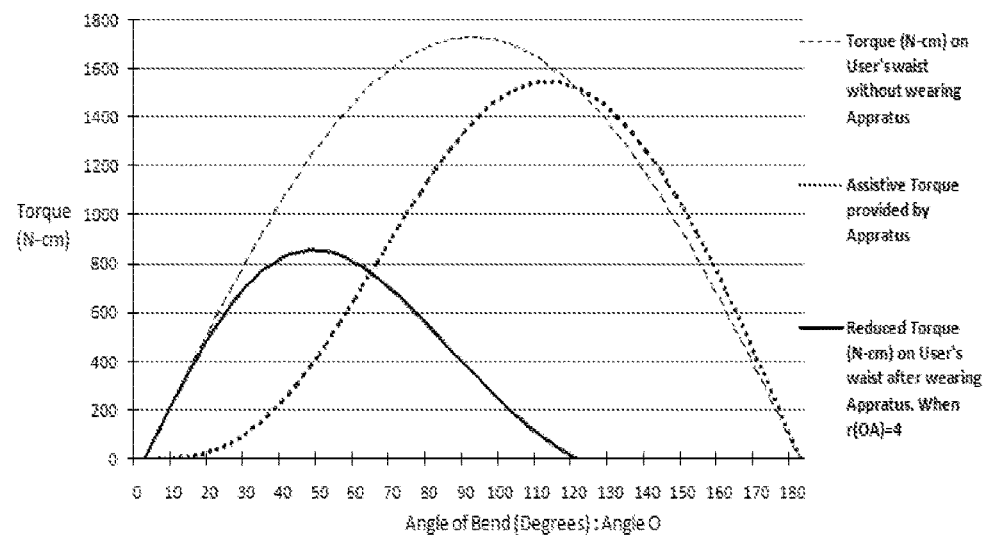
FIG. 10 illustrates results for torque and load when a user incorporates the apparatus with lever arm length 4 cm in accordance with an embodiment of the present subject matter.

Referring to FIG. 10, wherein a representation of non-linear variation of torque with respect to the angle of bend is illustrated and a reduction of load on user's waist is represented with torque on abscissa and angle of bend on ordinate is illustrated as an embodiment of the present subject matter. Following Table 4 represents a data of a user with 70 kg self-weight with height 180 cm and lifting a load of 20 kg with lever arm of 4 cm.

TABLE 4

| Sr. No. | Angle ° (degrees) | Load (N-cm) on User's waist without wearing apparatus+ | Assistive Torque provided by Apparatus | Reduced Load (N-cm) on User's waist after wearing apparatus. When r(OA) = 4 |
|---|---|---|---|---|
| 1 | 0 | 0 | 0.00 | 0 |
| 2 | 30 | 865 | 126 | 739 |
| 3 | 60 | 1499 | 713 | 786 |
| 4 | 90 | 1731 | 1377 | 354 |
| 5 | 120 | 1499 | 1511 | −12 |
| 6 | 150 | 866 | 967 | −101 |
| 7 | 180 | 0 | 0 | −0 |

In an implementation, after observing the above data from Table 1 to Table 4, it may be concluded that the maximum torque may be obtained at lever arm 4 cm which may provide a maximum arm length thus resulting in a maximum torque. In addition to the maximum torque, a maximum torque at each lever arm length may be observed at angle 80-110 degrees.

In an exemplary embodiment of the invention the apparatus may be employed in the fields or situations comprising:
1) Defense forces in which the soldiers in the army are subjected to constant running, bending, crawling and sometimes in an extraordinary uncomfortable position;
2) Construction sites wherein the labourers and technicians are in activities comprising bending and retracting while carrying heavy loads and other positions like drilling at extreme low or high positions, hammering and the like;
3) Person who is responsible for the household work such as a home-maker who performs all tasks in which many musculoskeletal activities like bending, kneeling, and the like;
4) All kinds of industries wherein the workers have to carry heavy loads like work piece or work jobs on machines like lathe, drilling and milling;
5) Old age people whose bone are degraded by low calcium content and thus require support for walking, bending, sitting down, standing up;
6) In agriculture wherein the farmers have to constantly bend down for piercing seeds in the ground and carrying heavy loads for storage in warehouse;
7) In medical fields in which patients with kyphosis, spondylitis and other similar disorder where they find uncomfortable to bend and sit.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible. The present invention can be embodied in many other forms or carried out in other ways, without departing from the spirit or essential characteristics thereof, and the above mentioned embodiment of the invention have been disclosed in detail only for illustrative purposes. It is understood that the invention is not limited thereto, but is susceptible of numerous changes and modifications as known to those skilled in the art, and all such variations or modifications of the disclosed apparatus, including the rearrangement of parts, lie within the scope of the present invention.

I claim:

1. A single point torque adjusting mechanical assembly, for assisting musculoskeletal activities, characterized in that the said assembly comprising of:
   an upper element (101');
   a lower element (102');
   a resilient means (105') with fixed end and free end (119');
   a flexible inextensible element or rope (114');
   a hinge pin (110') and a shaft (118');
   a load/torque adjusting means (108') having a single point at its free end (116');
   wherein the assembly varies the torque non-linearly by adjusting a lever arm length such that fixed end of the resilient means 105' need not be displaced;
   wherein the upper element (101') is moveably secured with lower element (102') by the hinge pin (110') and shaft (118'), and one end of the load adjusting means (108) is moveably connected with a secured end of upper element (101'),
      wherein the flexible inextensible element or rope (114') is moveably secured with/between the free end (119') of the resilient means (105') and hinge pin (110') and such flexible inextensible element (114') passes through the free end (116') of the load adjusting means (108'), wherein the length of the flexible inextensible element or rope (114') is equivalent or equal to sum of distance between the hinge pin (110') and the free end (116') of load adjusting means (108') and distance between free end (116') of load adjusting means (108') and the free end (119') of the resilient means (105'), wherein the sum of such distance remains constant; and
   wherein the said load adjusting means (108') slides over lower end of the upper element (101') and the lower element (102') to change lever arm length to produce non-linear variable counter torque.

2. The single point torque adjustment mechanical assembly as claimed in claim 1, wherein the hinge pin (110') and the shaft (118') is replaceable by a ball and socket joint.

3. The single point torque adjusting mechanical assembly as claimed in claim 1, wherein the torque is adjusted without adjusting pre load/tension in the resilient means (105').

4. The single point torque adjusting mechanical assembly as claimed in claim 1, wherein the load adjusting means (108') is locked/unlocked with lower end of the upper element (101') using engagement/disengagement means (109').

5. The single point torque adjusting mechanical assembly as claimed in claim 1, wherein the said assembly optionally comprises of an extended mechanism to facilitate locking/unlocking and sliding of load adjusting means (108') to adjust the torque.

6. A method for single point torque adjustment mechanical assembly, for assisting musculoskeletal activities, wherein the single point torque adjustment mechanical assembly comprises an upper element (101');
   a lower element (102');
   a resilient means (105') with fixed end and free end (119');
   a flexible inextensible element or rope (114');
   a hinge pin (110'), a shaft (118'); and
   a load/torque adjusting means (108') having a single point at its free end (116') characterized in that the method comprising:
      varying, torque by adjusting lever arm length and without displacing fixed end of resilient means (105') by,
      securing, the upper element (101') with the lower element (102') by the hinge pin (110') and the shaft (118');
      connecting, one end of the load adjusting means (108') with a secured end of the upper element (101');
      securing, the flexible inextensible element or rope (114') with/between the free end (119') of the resilient means (105') and the hinge pin (110');
      passing the flexible inextensible element or rope (114') through the free end (116') of the load adjusting means (108'), wherein the length of the flexible inextensible element or rope (114') is equivalent or equal to sum of distance between the hinge pin (110') and the free end (116') of the load adjusting means (108') and distance between the free end (116') of load adjusting means (113') and the free end (119') of the resilient means (105'), wherein the sum of such distance remains constant; and
      sliding, the said load adjusting means (108') over lower end of the upper element (101') and the lower element (102') to change lever arm length in order to produce non-linear variable counter torque.

7. An apparatus for assisting musculoskeletal activities characterized in that the said apparatus comprising:
   one or more longitudinal mechanical elements;
   one or more adjustable hinge mechanism means (104);
   one or more single point torque/load adjustment mechanical assembly (113), wherein the mechanical assembly (113) comprises an upper element (101), a lower element (102'), a resilient means (105') with fixed end and free end (119'), a flexible inextensible element or rope (114'), a hinge pin (110') and a shaft (118') and a load/torque adjusting means (108') having a single point at its free end (116');
      wherein the assembly varies the torque non-linearly by adjusting a lever arm length such that fixed end of the resilient means (105') need not be displaced;
      wherein the upper element (101') is moveably secured with lower element (102') by the hinge pin (110') and shaft (118'), and one end of the load adjusting means (108') is moveably connected with a secured end of upper element (101');
      wherein the flexible inextensible element or rope (114') is moveably secured with/between the free end (119') of the resilient means (105') and hinge pin (110') and such flexible inextensible element (114') passes through the free end (116') of the load adjusting means (108'), wherein the length of the flexible inextensible element or rope (114') is equivalent or equal to sum of distance between the hinge pin (110') and the free end (116') of the load adjusting means (108') and distance between the free end (116') of load adjusting means (108') and the free end (119') of the resilient means (105'), wherein the sum of such distance remains constant; and
      wherein the said load adjusting means (108') slides over lower end of the upper element (101') and the lower element (102') to change lever arm length to produce non-linear variable counter torque;
   an arrangement for flexibility and height adjustment means (115);
   one or more waist straps/belts (111), back (107) or shoulders straps (106); and
   one or more body adaptable shoulder element (101), one or more thigh element 102;
wherein the apparatus enables a user to share load on body parts and overcome effort required to return to a neutral position by employing a counter torque by storing potential energy in a resilient means (105),
the counter torque is developed when the user alters from the neutral position by performing musculoskeletal activities which is a result of the potential energy stored in the resilient means (105);
   wherein the single point torque/load adjustment mechanical assembly (113) incorporated with the adjustable hinge means (104) attached to the resilient means (105) is responsible for generating the counter torque to bring back the user to the neutral position;
wherein the counter torque varies non-linearly by adjusting longitudinal distance between hinge pin (110) of hinge (104) and single point (116) wherein the shaft (118) acts as an axis of rotation and the said longitudinal distance acts as a lever arm.

8. The apparatus as claimed in claim 7 wherein the apparatus further comprises shoulder cushion straps (106), knee cups and a waist belt (111) for gripping the apparatus to user's body.

9. The apparatus as claimed in claim 7 wherein the potential energy of the resilient means (105) exerts a force at the hinge (104), producing the torque with the single point torque/load adjustment mechanical assembly (113) and further provides assistive torque when the user puts a step or action while walking, bending, sitting, kneeling, rotating.

10. The apparatus as claimed in claim 7 wherein the apparatus optionally comprises of an extended mechanism to facilitate locking/unlocking and sliding of load adjusting means (108) to adjust the torque.

11. The apparatus as claimed in claim 7 wherein the mechanical assembly (113) adjusts the load and assistive torque at waist and knee joints to maximum and minimum in accordance with bending angle and wherein the adjustment of the assistive torque to maximum and minimum provides support when the load is maximum and minimum, respectively, at the knee and the waist joints, wherein pattern and profile of the assistive torque is adjustable.

12. The apparatus as claimed in claim 7 wherein the apparatus further enables proper human posture of the user and corrects spinal deformation of the user.

13. A leg apparatus for assisting musculoskeletal activities characterized in that the said apparatus comprising:
   one or more longitudinal mechanical elements (103);
   one or more adjustable hinge means (104);

one or more single point torque/load adjustment mechanical assembly (113), wherein the mechanical assembly (113) comprises an upper element (101), a lower element (102'), a resilient means (105') with fixed end and free end (119'), a flexible inextensible element or rope (114'), a hinge pin (110') and a shaft (118') and a load/torque adjusting means (108') having a single point at its free end (116');
    wherein the assembly varies the torque non-linearly by adjusting a lever arm length such that fixed end of the resilient means (105') need not be displaced;
    wherein the upper element (101') is moveably secured with lower element (102') by the hinge pin (110') and shaft (118'), and one end of the load adjusting means (108') is moveably connected with a secured end of upper element (101');
    wherein the flexible inextensible element or rope (114') is moveably secured with/between the free end (119') of the resilient means (105') and hinge pin (110') and such flexible inextensible element (114') gasses through the free end (116') of the load adjusting means (108'), wherein the length of the flexible inextensible element or rope (114') is equivalent or equal to sum of distance between the hinge pin (110') and the free end (116') of the load adjusting means (108') and distance between the free end (116') of load adjusting means (108') and the free end (119') of the resilient means (105'), wherein the sum of such distance remains constant; and
    wherein the said load adjusting means (108') slides over lower end of the upper element (101') and the lower element (102') to change lever arm length to produce non-linear variable counter torque;
    one or more cushioned straps (117);
    optionally one or more foot elements (120); and
    an arrangement for flexibility and height adjustment means (115);
wherein the leg apparatus enables a user to share load on knees/legs and overcome effort required to return leg and knee joint in neutral position by employing a counter torque by storing potential energy in the resilient means (105) and directing load to ground
wherein the counter torque is developed when the user alters from the neutral leg position by performing musculoskeletal activities which is a result of the potential energy stored in the resilient means (105);
wherein the single point torque/load adjustment mechanical assembly (113) incorporated with an adjustable hinge means (104) attached to the resilient means (105) generates the counter torque in order to bring back the user's leg to the neutral position
wherein the counter torque varies non-linearly by adjusting longitudinal distance between hinge point (110) of hinge means (104) and a single point (116) of the load adjusting means (108), wherein the shaft (118) of the adjustable hinge means (104) acts as an axis of rotation and said longitudinal distance acts as lever arm;
wherein the load/weight is transferred to the ground via the one or more foot elements (120).

14. An apparatus for assisting musculoskeletal activities characterized in that the said apparatus comprising:
    one or more waist straps/belts (111), back (107) or shoulder straps (106); and
        a mechanical assembly (113) and a structure (601) having a body adaptable shaped profile to carry loads;
    wherein the mechanical assembly (113) comprises an upper element (101), a lower element (102'), a resilient means (105') with fixed end and free end (119'), a flexible inextensible element or rope (114'), a hinge pin (110') and a shaft (118') and a load/torque adjusting means (108') having a single point at its free end (116');
    wherein the assembly varies the torque non-linearly by adjusting a lever arm length such that fixed end of the resilient means (105') need not be displaced;
    wherein the upper element (101') is moveably secured with lower element (102') by the hinge pin (110') and shaft (118'), and one end of the load adjusting means (108') is moveably connected with a secured end of upper element (101');
    wherein the flexible inextensible element or rope (114) is moveably secured with/between the free end (119') of the resilient means (105') and hinge pin (110') and such flexible inextensible element (114') passes through the free end (116') of the load adjusting means (108'), wherein the length of the flexible inextensible element or rope (114') is equivalent or equal to sum of distance between the hinge pin (110') and the free end (116') of the load adjusting means (108') and distance between the free end (116') of load adjusting means (108') and the free end (119') of the resilient means (105'), wherein the sum of such distance remains constant; and
    wherein the said load adjusting means (108') slides over lower end of the upper element (101' and the lower element (102') to change lever arm length to produce non-linear variable counter torque;
    wherein the apparatus enables a user to share load on body parts and transfer such load to ground;
    wherein an upper side of structure (601) is mounted at a back strap (107) using moveable securing means wherein the structure (601) forms a platform or a cantilever beam which transmits load at the head to the belt and further the belt transfers the load legs and finally to the ground.

15. The apparatus as claimed in claim 13, wherein multi-dimensional hinge (603) enables the structure (601) to remain in vertical orientation irrespective of the posture of the user.

16. A method of varying torque of mechanical assembly used in an apparatus for assisting musculoskeletal activities, wherein the apparatus comprises single point torque/load adjustment assembly (113) and a structure (601), wherein the mechanical assembly (113) comprises an upper element (101), a lower element (102'), a resilient means (105') with fixed end and free end (119'), a flexible inextensible element or roe (114'), a hinge pin (110') and a shaft (118') and a load/torque adjusting means (108') having a single point at its free end (116');
    wherein the method is characterized in varying, torque by adjusting lever arm length and without displacing fixed end of resilient means (105') by;
        securing, the upper element (101') with lower element (102') by the hinge pin (110') and shaft (118');
        connecting, one end of the load adjusting means (108') with a secured end of upper element (101');
        securing, the flexible inextensible element or rope (114') with/between the free end (119') of the resilient means (105') and the hinge pin (110');
        passing, the flexible inextensible element or rope (114') through the free end (116') of the load adjusting means (108'), wherein the length of the flexible inextensible element or rope (114') is equivalent or equal to sum of distance between the hinge pin (110') and the free end (116') of the load adjusting means (108') and distance between the free end (116') of load adjusting means (113') and the free end (119') of the resilient means (105'), wherein the sum of such distance remains constant; sliding, the said load adjusting means (108') over lower end of the upper element (101') and the lower element (102') to change lever arm length in order to produce non-linear variable counter torque, wherein the method is further characterized in:

enabling, a user to share load on body parts and overcome effort required to return to neutral position by employing a counter torque by storing potential energy in the resilient means (105) and directing the load to ground by developing, counter torque by the single point torque/load adjustment assembly (113)

when the user alters from the neutral position by performing musculoskeletal activities, using of the potential energy stored in the resilient means (105);

generating, the counter torque by the single point torque/load adjustment mechanical assembly (113) incorporated with adjustable hinge (104) attached to the resilient means (105) in order to bring back the user to the neutral position;

adjusting, longitudinal distance between of the hinge (104) and the single point torque/load adjustment mechanical assembly (113) in order to vary the counter torque non-linearly, wherein the hinge (104) acts as an axis of rotation and said longitudinal distance acts as a lever arm;

wherein the structure (601) to share and direct the load from head and neck, and the back does share and direct the load form head, neck and back to waist of the user and ground.

* * * * *